Figure 1:
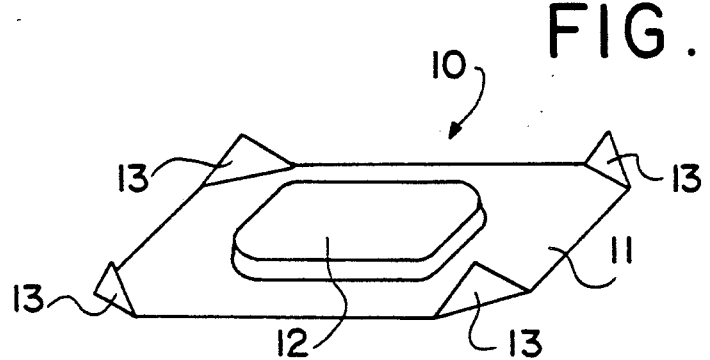

United States Patent [19]

Anhäuser et al.

[11] Patent Number: 5,115,913

[45] Date of Patent: May 26, 1992

[54] PACKAGED SUPPORTED PRESSURE-SENSITIVE ADHESIVE PLASTERS

[75] Inventors: Dieter Anhäuser, Melsbach; Ralf Huhn, Königswinter, both of Fed. Rep. of Germany

[73] Assignee: LTS Lohmann Therapie-Systeme GmbH & Co. KG, Neuwied, Fed. Rep. of Germany

[21] Appl. No.: 543,637

[22] Filed: Jun. 26, 1990

[30] Foreign Application Priority Data

Jun. 30, 1989 [DE] Fed. Rep. of Germany ....... 3921434

[51] Int. Cl.⁵ .................. B65D 57/00; A61B 19/02
[52] U.S. Cl. .................. 206/447; 206/440; 206/813
[58] Field of Search ........ 206/460, 447, 497, 494, 206/511, 454, 449, 813, 440

[56] References Cited

U.S. PATENT DOCUMENTS

| | | | |
|---|---|---|---|
| 2,049,030 | 7/1936 | Strauss | 206/813 X |
| 2,338,749 | 1/1944 | Wilbur | 206/813 X |
| 2,666,523 | 1/1954 | Ryan et al. | 206/497 X |
| 2,974,787 | 3/1961 | Cooper | 206/367 |
| 4,251,712 | 2/1981 | Parr | 206/447 X |
| 4,440,301 | 4/1984 | Intengan | 206/504 X |
| 4,978,007 | 12/1990 | Jacobs et al. | 206/813 X |

*Primary Examiner*—Bryon P. Gehman
*Attorney, Agent, or Firm*—Sprung Horn Kramer & Woods

[57] ABSTRACT

In combination, a bag, at least one active mass, and a support, the active mass being carried on the support within the bag and having an exposed pressure-sensitive adherent surface, the support carrying integral spacers which are laterally spaced from the active mass and project above the surface of the support a distance greater than the height of said active mass, thereby to space the mass from the bag.

10 Claims, 2 Drawing Sheets

PACKAGED SUPPORTED PRESSURE-SENSITIVE ADHESIVE PLASTERS

DESCRIPTION

The present invention relates to a device for increasing the storage stability of sheet-like substrate sections being packed in bags and rendered pressure-sensitive adhesive, the pressure-sensitive surface of which being protected by a supporting layer protecting said pressure-sensitive adhesive surface at least partially, and in which agglutination of the supporting layer with the packing arises caused by migration of the pressure-sensitive adhesive due to cold flow, and to the use thereof.

The production and use of sheet-like pressure-sensitive adhesive substrate sections is known. In this connection, it is frequently necessary to protect the sections from evaporation of volatile components during the time between production and application thereof. This can be managed in that the pressure-sensitive adhesive substrate sections, after protection of their pressure-sensitive adhesive surface by a removable supporting layer, are occluded or sealed within a bag. In most cases the carrier layer projects from the pressure-sensitive adhesive surface in order to facilitate the removal of the carrier layer prior to application. However, the disadvantage of such a design is the fact that during storage of substrate sections packed in such a way, due to cold creep of the pressure-sensitive adhesive, pressure-sensitive adhesive escapes around the substrate section; this leads to agglutination with the packing surfaces so that taking the laminate out of a package opened at only one side becomes difficult, or even impossible.

Up to now, the solution of this problem was only found by inserting a polymeric foil which—as a matter of fact—in addition to extra expenses with respect to material, also poses technical problems.

It is accordingly the object of the present invention to provide a simple device for increasing the storage stability of sheet-like pressure-sensitive adhesive substrate sections packed in bags, the pressure-sensitive adhesive surface of said sections being protected by a supporting layer, which at least partially projects over the pressure-sensitive adhesive surface, agglutination of the supporting layer with the packing caused by migration of the pressure-sensitive adhesive due to cold flow thereby being prevented.

Unexpectedly, this object is achieved by promoting elevations serving as spacers between carrier layer and packing in the portion of the carrier layer extending the pressure-sensitive adhesive surface, said elevations being fixed on the carrier layer or formed of the carrier layer itself.

The present invention includes two basic possibilities. On the one hand, the spacers can be created by adding foreign substances, on the other one by utilizing the carrier layer itself. In the first case, the spacers are formed by applying hot-melt-polymers which are firmly anchored to the supporting layer after cooling, or non-adhesive materials are fixed on the carrier layer by means of a permanent adhesive. In the latter case, the projecting surfaces of the supporting material are deformed by folding, embossing, or deep-drawing in such a way that elevations are created in the direction of the packing surface adjacent to the substrate section, which serve as spacers. This can be achieved, for example, by folding over edges of the supporting layer, or by bending tabs obtained by cutting in the sides of said carrier layer. A further possibility is to emboss or deep-draw knobs in the projecting part of the supporting layer, which knobs extend in the direction of the packing surface adjacent to the substrate section. Webs or fins can also serve as spacers. The webs are formed by embossing or deep-drawing the projecting part of the supporting layer, and they corner around edges of the substrate section, or coherently run parallel to the borders of the substrate section. As a matter of fact, there can be multiple arrangements of substrate sections on the supporting layer.

The carrier material forming the supporting layer may also be multi-layered and must be arranged relative to the pressure-sensitive adhesive surface of the substrate section in such a way that the removal of the substrate section is possible. In all cases where the spacers are formed of the supporting layer itself, the supporting layer has to exhibit permanent hot or cold deformability. In this connection, suitable materials, e.g., are thermoplastic polymers, metals, or a combination of the two materials.

The formation of the spacers can be carried out prior or after application of the substrate section on the supporting layer, whereby the substrate section may be of any shape. The height of the spacers is substantially determined by the thickness of the substrate section.

The device according to the present invention is particularly used in the packaging of either a plaster or a transdermal therapeutic system having an exposed pressure-sensitive adhesive surface, which may be generally characterized as an active mass.

The invention will be further illustrated, by way of example only, in the following description with reference to the accompanying drawings. FIGS. 1 to 5 illustrate the invention without representation of the packing.

Figure 4:
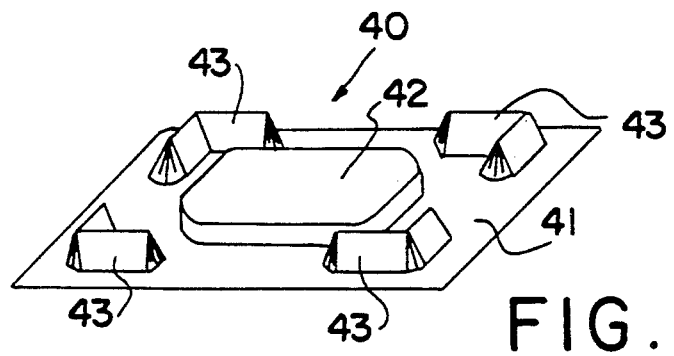
Figure 5:
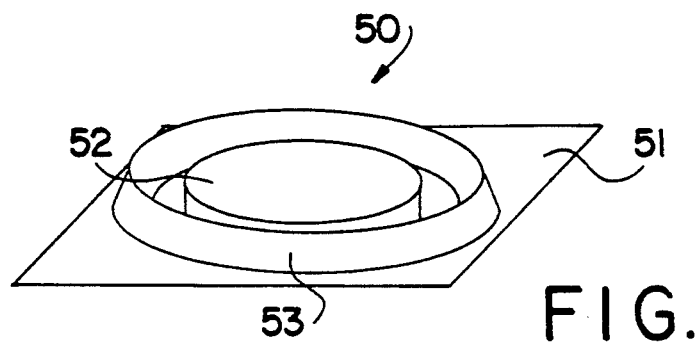
Figure 6:
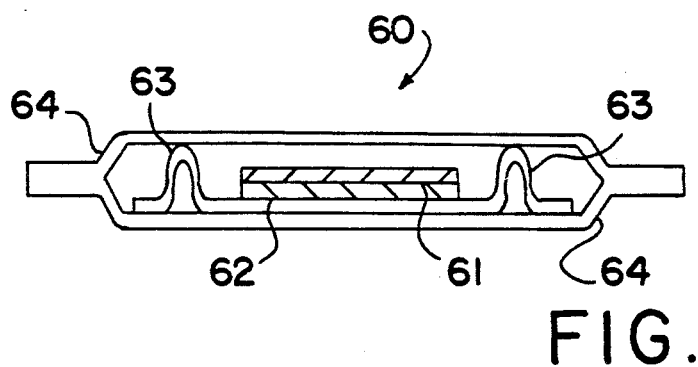

FIG. 1 illustrates a perspective representation of an embodiment according to the present invention, FIGS. 2 to 5 illustrate perspective representations of further embodiments according to the present invention, FIG. 6 is a section through a packed substrate section according to the present invention (not true to scale).

FIG. 1 shows a perspective representation 10 of an embodiment according to the present invention, in which a substrate section 12 is positioned on a supporting layer 11. The edges 13 of the extending portion of the supporting layer are bent upward and act as spacers.

Figure 2:
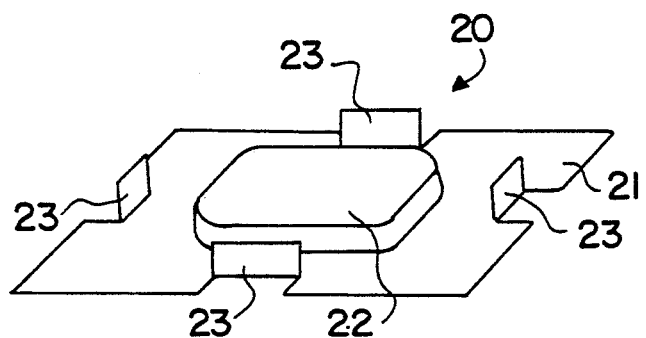

FIG. 2 shows an embodiment 20 according to the present invention, in which upwardly bent tabs 23 constitute the spacers, said tabs being formed by cutting-in the sides of he supporting material surface 21 projecting beyond the substrate section 22.

Figure 3:
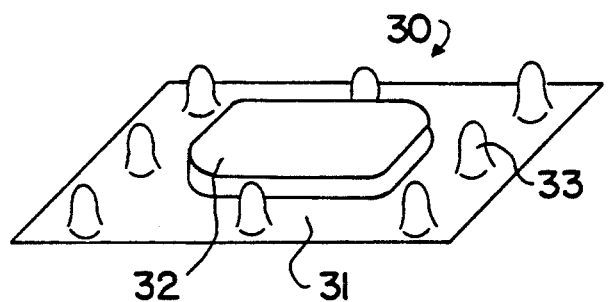

The arrangement 30 represented in FIG. 3 shows knobs 33 acting as spacers and being formed from the part of the supporting layer 31 projecting beyond substrate section 32.

In the arrangement 40 according to FIG. 4 webs of the portion 41 of the supporting layer projecting beyond the substrate section 42 are shown cornering the edges of the substrate section and acting as spacers.

FIG. 5 represents an arrangement 50 in which a web 53 is formed by embossing or deep-drawing the projecting part 51 of the supporting layer runs parallel to the border of the substrate section 52 and effects the spacing.

FIG. 6 shows a cross-section 60 through a packaged substrate section 61 wherein the packaging surface 64 is kept apart from the supporting layer 62 by the spacer 63.

It is understood that the specification and examples re illustrative but not limitative of the present invention and that other embodiments within the spirit and scope of the invention will suggest themselves to those skilled in the art.

We claim:

1. In combination, a bag, an active mass, and a support, the active mass being carried on said support within said bag and having an exposed pressure-sensitive adhesive surface, the support being provided with means for spacing said adhesive surface from the bag, such spacing means comprising spacers integral with the support, said spacers being laterally spaced from the active mass and projecting above the surface of the support a distance greater than the height of said active mass.

2. A combination according to claim 1, wherein the support and spacers are formed of a hot-melt-polymer which is not tacky at room temperature.

3. A combination according to claim 1, wherein the spacers re formed by bending upwardly portions of the support spaced from the active mass.

4. A combination according to claim 3, wherein the upwardly bent portions are at angulated corners of the support.

5. A combination according to claim 3, wherein the support is provided with cuts which define the upwardly bent portions.

6. A combination according to claim 1, wherein the spacers are embossed or deep-drawn knobs in the support.

7. A combination according to claim 6, wherein the knobs are angulated.

8. A combination according to claim 6, wherein the knobs are substantially parallel with and substantially completely surround the active mass.

9. A combination according to claim 1, wherein the active mass is an adhesive plaster.

10. A combination according to claim 1, wherein the active mass is a transdermal therapeutic.

* * * * *

UNITED STATES PATENT AND TRADEMARK OFFICE
CERTIFICATE OF CORRECTION

PATENT NO. : 5,115,913

DATED : May 26, 1992

INVENTOR(S) : Anhauser et al.

It is certified that error appears in the above-identified patent and that said Letters Patent is hereby corrected as shown below:

Col. 4, line 5   Delete " re " and substitute -- are --

Signed and Sealed this

Twenty-sixth Day of October, 1993

Attest:

BRUCE LEHMAN

Attesting Officer    Commissioner of Patents and Trademarks